(12) United States Patent
Montoya-Barreto et al.

(10) Patent No.: US 9,556,409 B2
(45) Date of Patent: Jan. 31, 2017

(54) BIOREACTOR TO OBTAIN BIOACTIVE SUBSTANCES THROUGH SOLID-STATE FERMENTATION USING MACROMYCETES FUNGI

(71) Applicant: Universidad de Caldas, Manizales (CO)

(72) Inventors: Sandra Montoya-Barreto, Caldas (CO); Oscar Julian Sanchez-Toro, Caldas (CO); Luis Fernando Gutierrez Mosquera, Caldas (CO)

(73) Assignee: Universidad de Caldas, Manizales (CO)

( * ) Notice: Subject to any disclaimer, the term of this patent is extended or adjusted under 35 U.S.C. 154(b) by 0 days.

(21) Appl. No.: 13/865,035

(22) Filed: Apr. 17, 2013

(65) Prior Publication Data

US 2015/0197718 A1    Jul. 16, 2015

(30) Foreign Application Priority Data

Apr. 17, 2012   (CO) .................................. 12/063251

(51) Int. Cl.
| | | |
|---|---|---|
| *C12M 1/00* | (2006.01) | |
| *C12M 3/00* | (2006.01) | |
| *C12M 1/16* | (2006.01) | |
| *C12M 1/12* | (2006.01) | |
| *C12M 1/06* | (2006.01) | |

(52) U.S. Cl.
CPC ............. *C12M 21/16* (2013.01); *C12M 23/04* (2013.01); *C12M 25/18* (2013.01); *C12M 27/06* (2013.01)

(58) Field of Classification Search
CPC ....... C12M 21/16; C12M 23/04; C12M 23/34; C12M 23/48
See application file for complete search history.

(56) References Cited

U.S. PATENT DOCUMENTS

| | | | | |
|---|---|---|---|---|
| 6,197,573 B1 | * | 3/2001 | Suryanarayan et al. ... | 435/286.7 |
| 6,620,614 B1 | * | 9/2003 | Luth et al. ................. | 435/291.3 |
| 6,797,508 B1 | * | 9/2004 | Holker ....................... | 435/252.1 |
| 7,476,534 B2 | * | 1/2009 | Wismar ..................... | 435/289.1 |

* cited by examiner

*Primary Examiner* — Nathan Bowers
(74) *Attorney, Agent, or Firm* — Hoglund & Pamias, PSC; Roberto J. Rios

(57) ABSTRACT

Fixed bed bioreactor with natural convection and forced draught to obtain bioactive substances by solid-state fermentation (SEF) using fungi macromycetes. This bioreactor may be from turn drum with pendulum motion and natural and forced convection to a tray bioreactor with natural convection. They are used in the production of bioactive substances as crude extracts of lignocellulosic enzymes and fungal polysaccharides obtained by using mixtures of lignocellulosic materials as substrates and macromycetes fungi as inoculum, controlling pH, humidity and particle size, inoculation rate and environmental conditions during fermentation such as temperature, relative humidity and carbon dioxide and oxygen concentration.

16 Claims, 10 Drawing Sheets

BIOREACTOR TO OBTAIN BIOACTIVE SUBSTANCES THROUGH SOLID-STATE FERMENTATION USING MACROMYCETES FUNGI

TECHNICAL FIELD

The present invention belongs to the field of mechanical engineering, specifically applied to industrial microbiology. It refers to a fixed bed bioreactor with natural convection and forced draft, with modifications for a rolling drum bioreactor with oscillating movement for natural and forced convection and a tray bioreactor with natural convention, which uses macromycetes fungi for obtaining lignocellulosic substrates and lignocellulosic enzymes by means of solid state fermentation (SSF) processes under controlled conditions.

BACKGROUND OF THE INVENTION

There is a market for bioreactors and solid-state fermentation processes for the production of lignocellulosic enzymes and polysaccharides testing different fungal and bacterial strains so as to quantify the potential of each biosubstance.

Fungal polysaccharides can de exo-polysaccharides and endo-polysaccharides and are obtained by submerged fermentation and solid-state fermentation (SSF). The exo-polysaccharides, those excreted from the culture medium, have been obtained specially by means of submerged fermentation processes; whereas by using solid state fermentation intra-polysaccharides are specially obtained, which are found inside diverse fruit bodies of the macromycetes fungi and the mycelium.

The fruit bodies of the fungi are obtained by the method of culture in a bag or bed on formulated substrates with different natural organic materials subjected to culturing conditions required for each species so as to obtain competitive yields for the market.

These methods present scaling problems due to the difficulty of controlling variables such as heat transfer (difficult dissipation), mass transfer (heterogeneous interaction between all the molecules and in all directions within the substrate). These processes have shown to be more efficient in the production of enzymes up to a pilot scale.

By using SSF with filamentous fungi it has been possible to obtain better yields in the production of enzymes, lower problems of growth inhibition by substrates and greater stability of the organisms to changes in temperature and pH than when these organisms are cultured in liquid medium, and a lower occurrence of enzyme degradation by the presence of undesirable proteases.

There is a need for technological development around SSF, to explore how to obtain new substances using filamentous fungi, exploring the physiological characteristics presented during the development of the fungal cells in SSF processes, such as the accumulation of glycerol, eritritol and arabinitol which generate gene induction in glycoamylases, perhaps due to the activity of water under these process conditions.

The formation of secondary metabolites of numerous filamentous fungi during SSF is associated to the formation of the aerial hyphase and spores at the beginning of the secondary metabolism phase and is only described in these types of processes and not in submerged fermentation.

One of the strongest reasons stopping the advances in SSF processes are the design and engineering problems for standardization and scaling limiting the reproducibility of the results.

Management of temperature, humidity, and substrate concentration gradients increases during the process, generating adverse conditions in stationary solid bed processes and rolling drum reactors or other equipment with intermittent agitation. The correlation between environmental conditions, such as oxygen concentration, humidity levels and temperature make it hard to regulate these parameters.

Fungal development under aerobic conditions in the bioreactor results in a considerable increase in the production of heat caused by a rapid raise in temperature. This effect is desirable in composting processes, but is totally undesirable in in biotechnological processes in bioreactors since a large part of the enzymes produced during SSF can denaturalize at the end of the process.

Thus, the present invention improves the conditions for controlling temperature, humidity and oxygen concentration achieving optimal conditions for the production of bioactive substances by means of solid-state fermentation.

SUMMARY OF THE INVENTION

The bioreactor of the present invention can vary from i) a fixed bed bioreactor with natural convection and forced draft, ii) a rolling drum bioreactor with pendulum motion and natural and forced convection, up to iii) tray bioreactor with natural convection; for producing bioactive substances as raw extracts of lignocellulosic enzymes and fungal polysaccharides obtained by means of solid state fermentation, using mixtures of lignocellulosic materials as substrates and macromycetes fungi as inoculate.

The process of producing biosubstances by means of solid state fermentation only uses various lignocellulosic residues as raw material, amongst which we can find residues from growth and post-production of coffee, sugar cane, wood, fruit trees, produce, legumes, oleaginous plants, and others. For the solid state fermentation process the physical and chemical variables of the substrates are taken into consideration, such as carbon-nitrogen ratio, concentration of minerals (calcium, magnesium, iron, zinc, manganese, and others), pH, humidity and particle size; similarly inoculation rate and environmental conditions during fermentation like temperature, relative humidity, carbon dioxide and oxygen concentration.

DETAILED DESCRIPTION OF THE INVENTION

Figure 5:
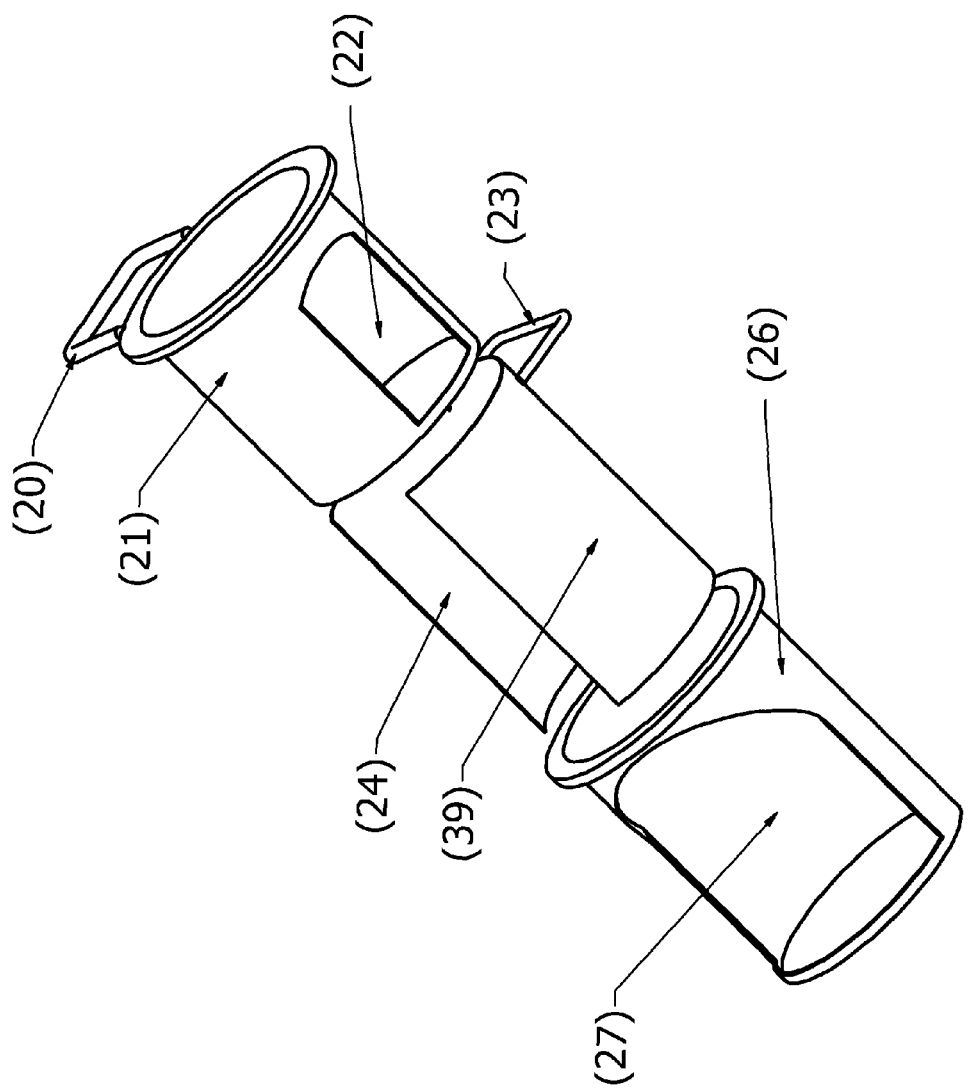
FIG. 5 shows the sampler, according to the present invention.

The body of the bioreactor (FIG. 1) is comprised of a stainless steel chamber (1) arranged with lateral spaces having a concave shape, a base diffuser (5) with a positive spin dispersion wall for distributing air and support for the boxes containing the substrate (FIG. 2), with valves for collecting the exudates and washing the equipment (2, 3), a main lid (28) provided with another lid that allows exchange of air with the outside (with a stainless steel mesh and a filter) (29), three peepholes for inspecting incubation of the substrates (4), two samplers with sample receiving chambers isolated form the external environment (8), shown in FIG. 5, a bottom air diffusor (31), two air ejectors (32), air mixer (33).

Figure 6:
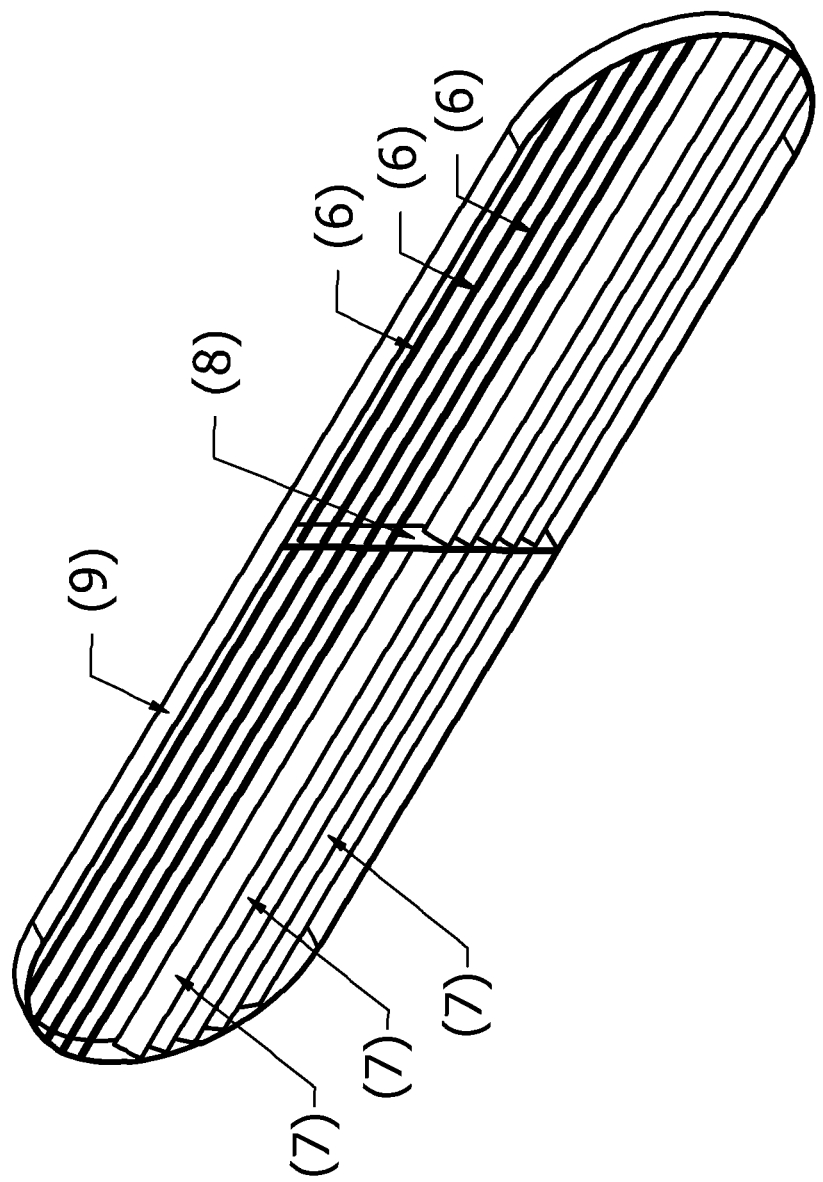
FIG. 6 shows the diffuser, according to the present invention.
Figure 9:
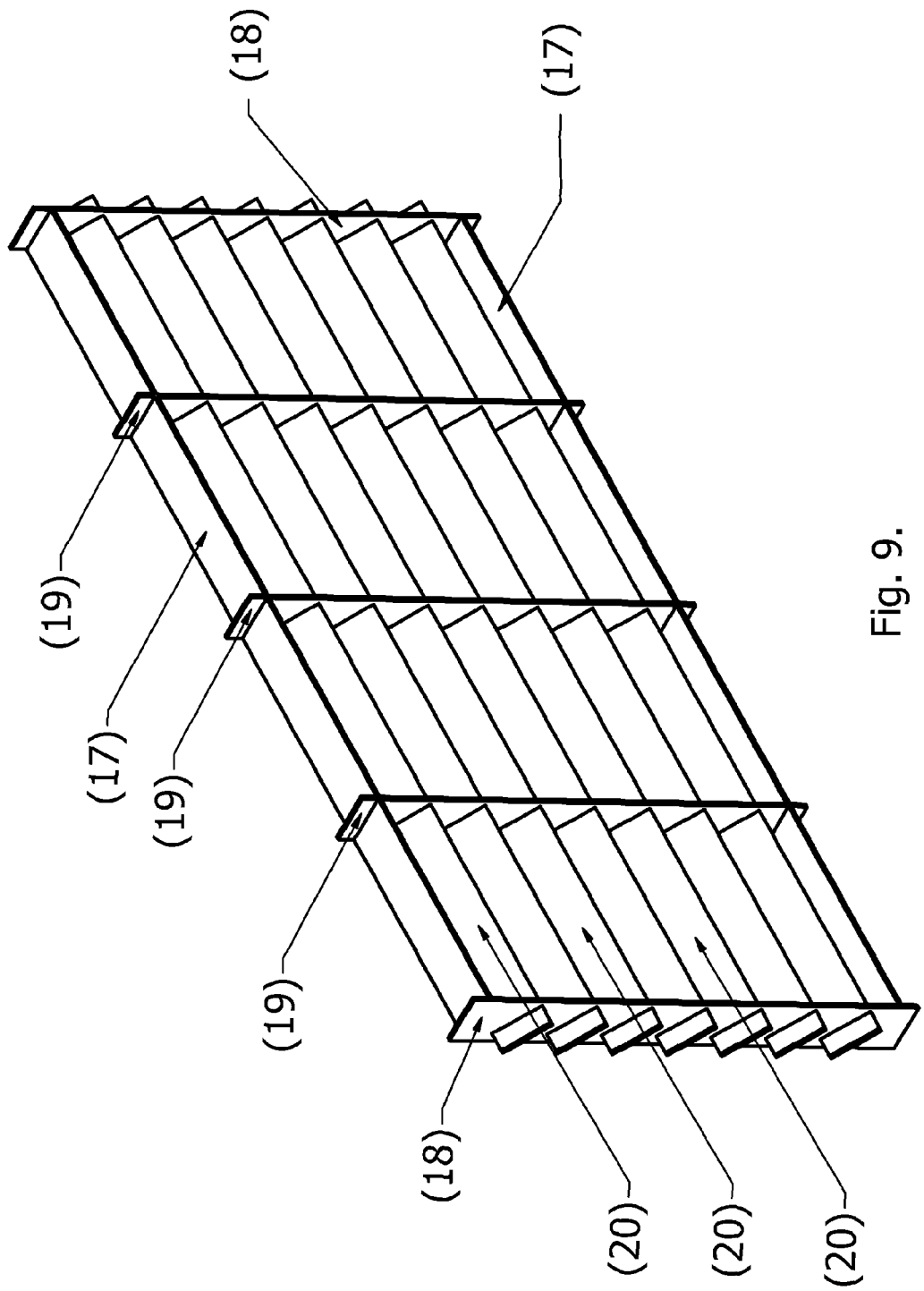
FIG. 9 shows the air diffuser system, according to the present invention.

Two bodies for the lateral air diffuser system (FIG. 6) and (FIG. 9) (9) each of them facing a combined positive (6) and negative (9) spin dispersion wall divide by a central partition wall (8) and a base diffuser (5) with a positive spin partition wall for distributing air when working with natural convention and directing the flow of air when the bioreactor is working with forced draft.

Three substrate containing boxes that can be disassembled comprise the fixed bed (10) are the ones supporting the fixed bed of substrate formulated with lignocellulosic materials and inoculated with a species of white or brown rot macromycetes, each having a 10 kg capacity. Each box is provided with hinges with a block (11, 12) on each side that allows for completely disassembling the box and releasing the block of substrate after incubation.

Figure 4:
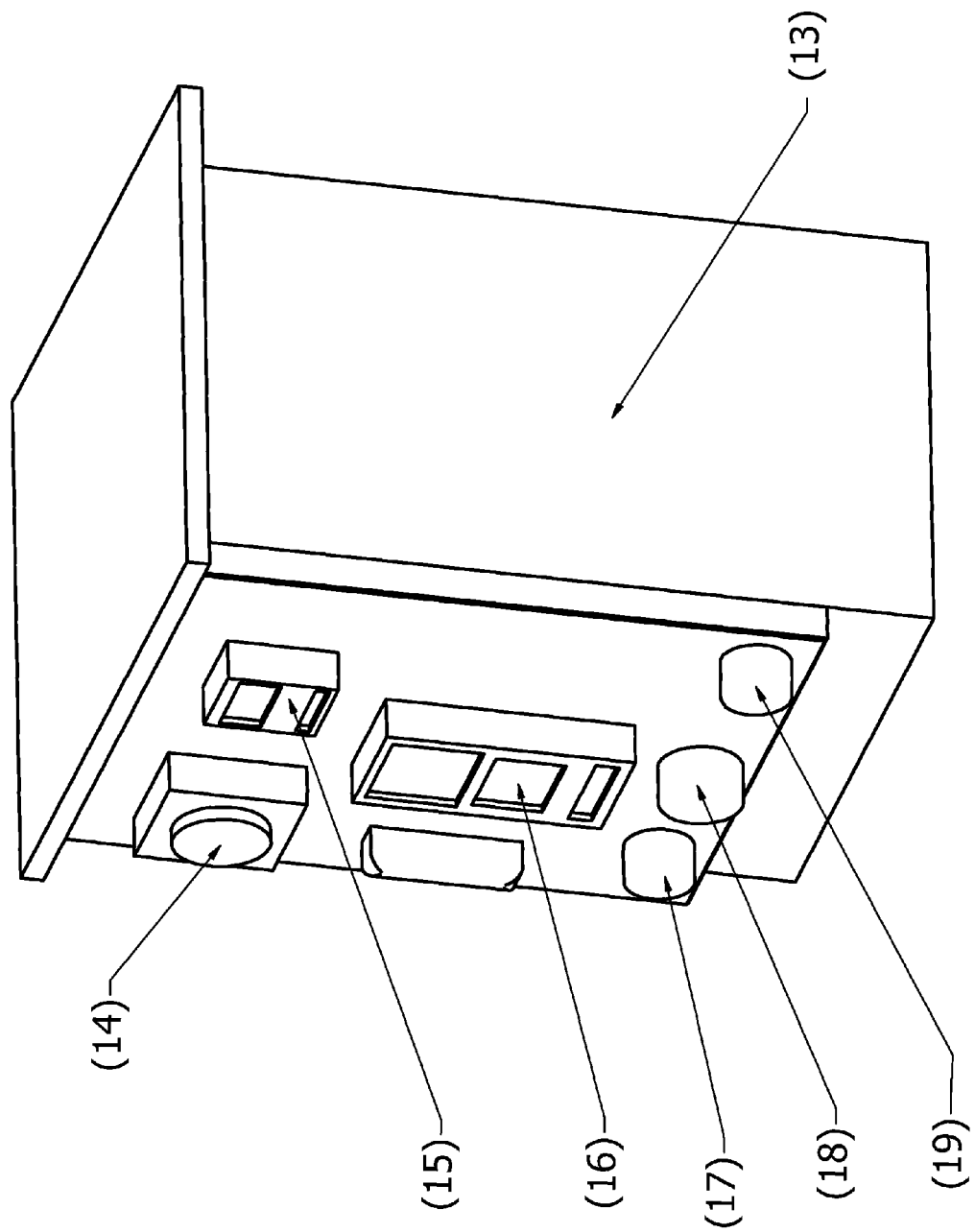
FIG. 4 shows the temperature and humidity control box, according to the present invention.

FIG. 4 shows a temperature and relative humidity control box (13) comprising a thermocouple selector (14), a monitor for 6 temperature points (15), a relative humidity monitor (16), power on indicator light (17), general switch (18), power off indicator light (19).

Two samplers (FIG. 5) provided with a fastening means (20), a main container for taking samples in contact with the environment (21), a main window for taking samples (22), a handle for the window controlling the entrance of air into the bioreactor (24), a valve controlling the entrance of air into the reactor (25), a general sampling container (26), an access window for the bioreactor (27).

Figure 3:
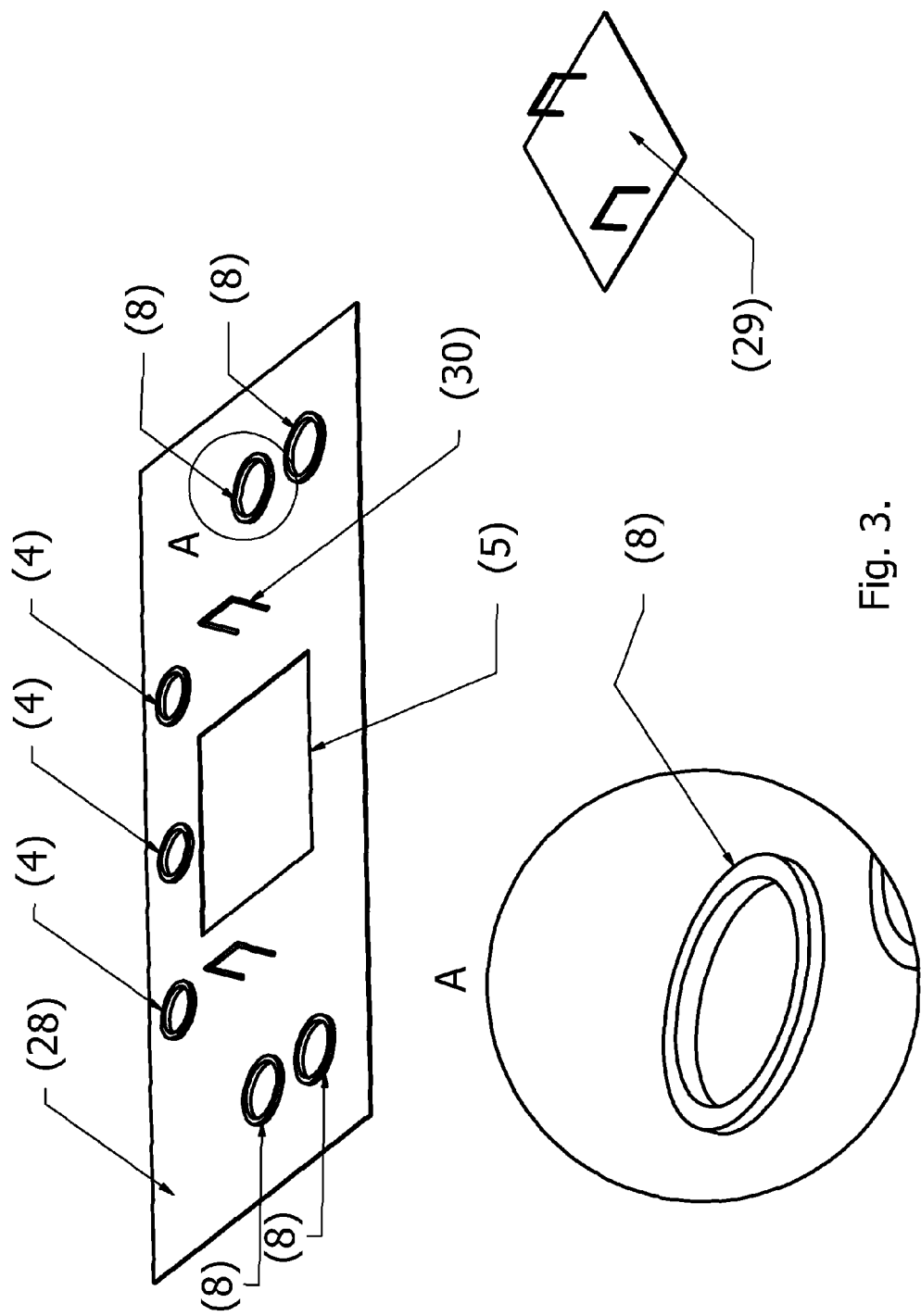
FIG. 3 shows the bioreactor's lid, according to the present invention.

FIG. 3 shows a bioreactor's lid (28), provided with three peepholes (4), two samplers 88), two handles (30) and a top lid for controlling the supply of oxygen and $CO_2$ (29).

Figure 7:
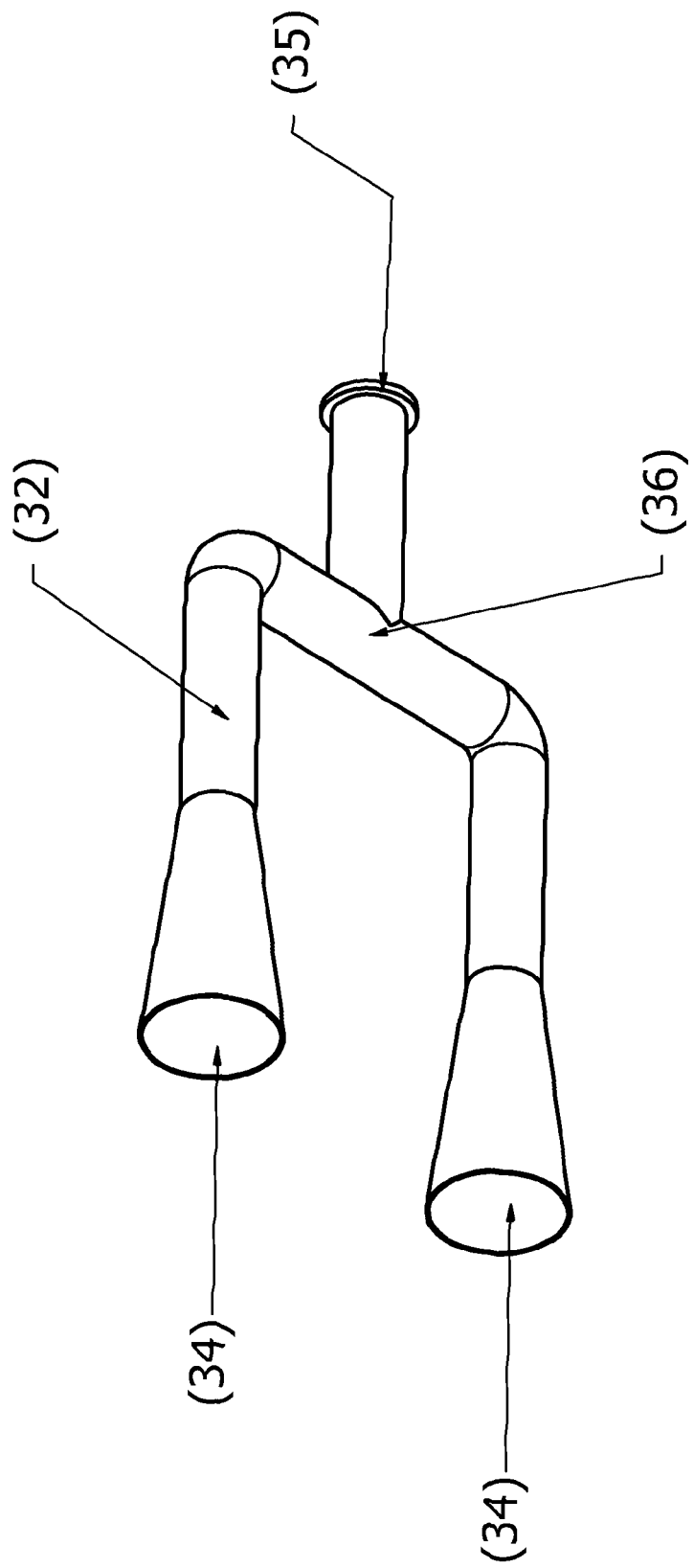
FIG. 7 shows the air ejectors, according to the present invention.

Two air ejectors (FIG. 7) (32) comprised of two air expanders (34), one air inlet (35) and an air duct (36).

Figure 8:
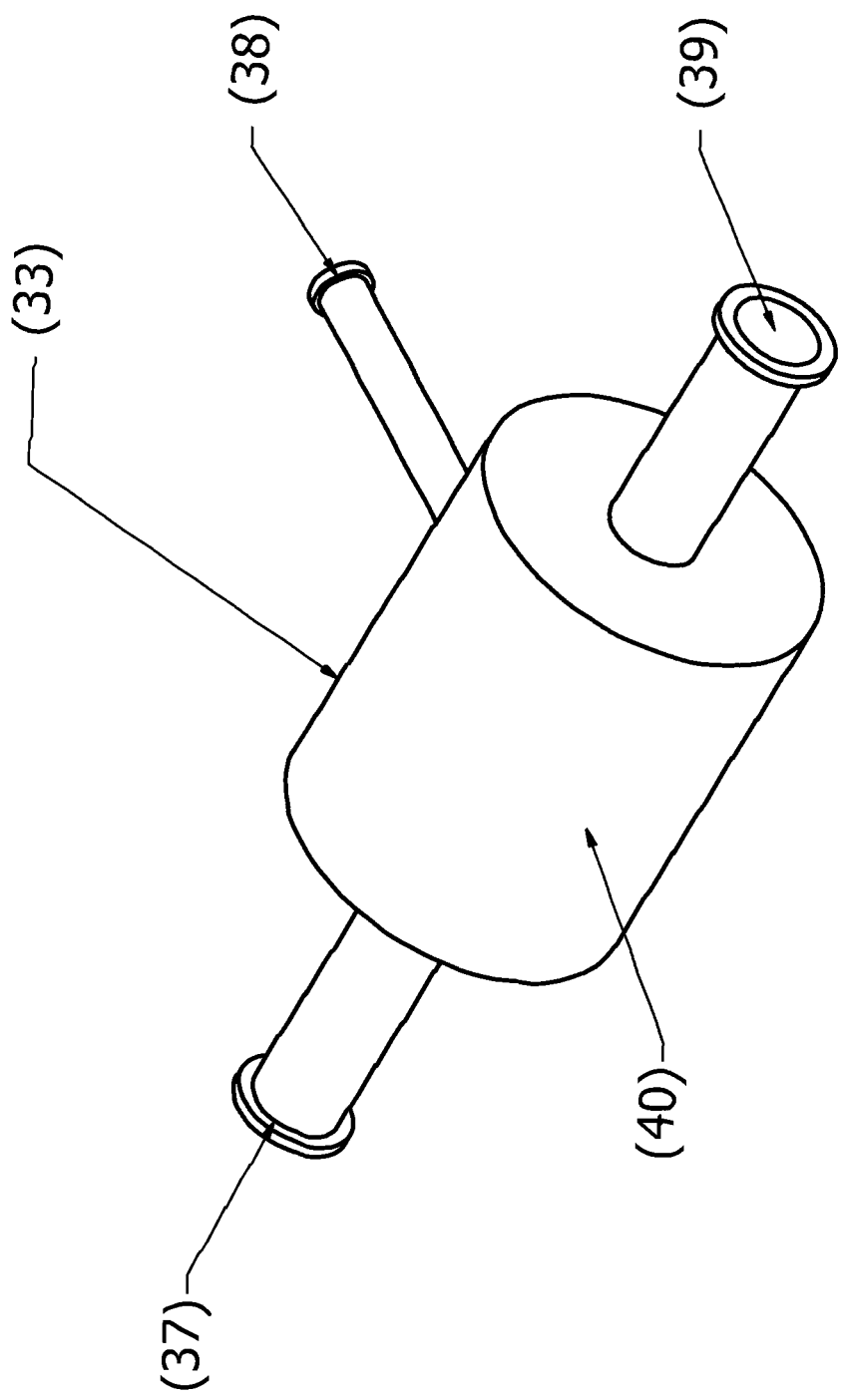
FIG. 8 shows the air mixer, according to the present invention.

FIG. 8 shows an air mixer (33) comprising a fresh air entrance (37), air recirculation (38), air exit towards the bioreactor (39) and a mixing tank for fresh and recycled air (40).

Figure 1:
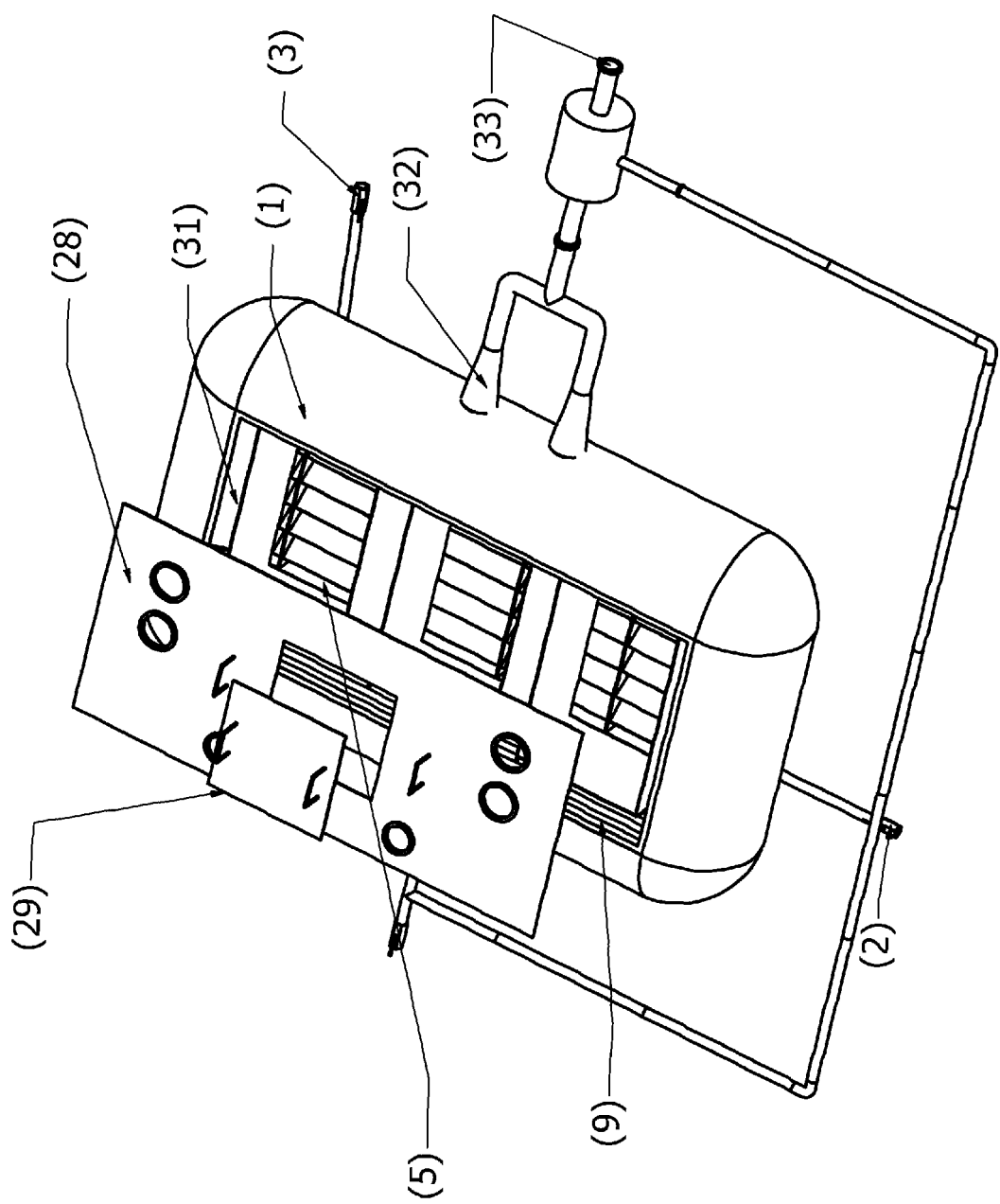
FIG. 1 shows the body of the bioreactor, according to the present invention.
Figure 2:
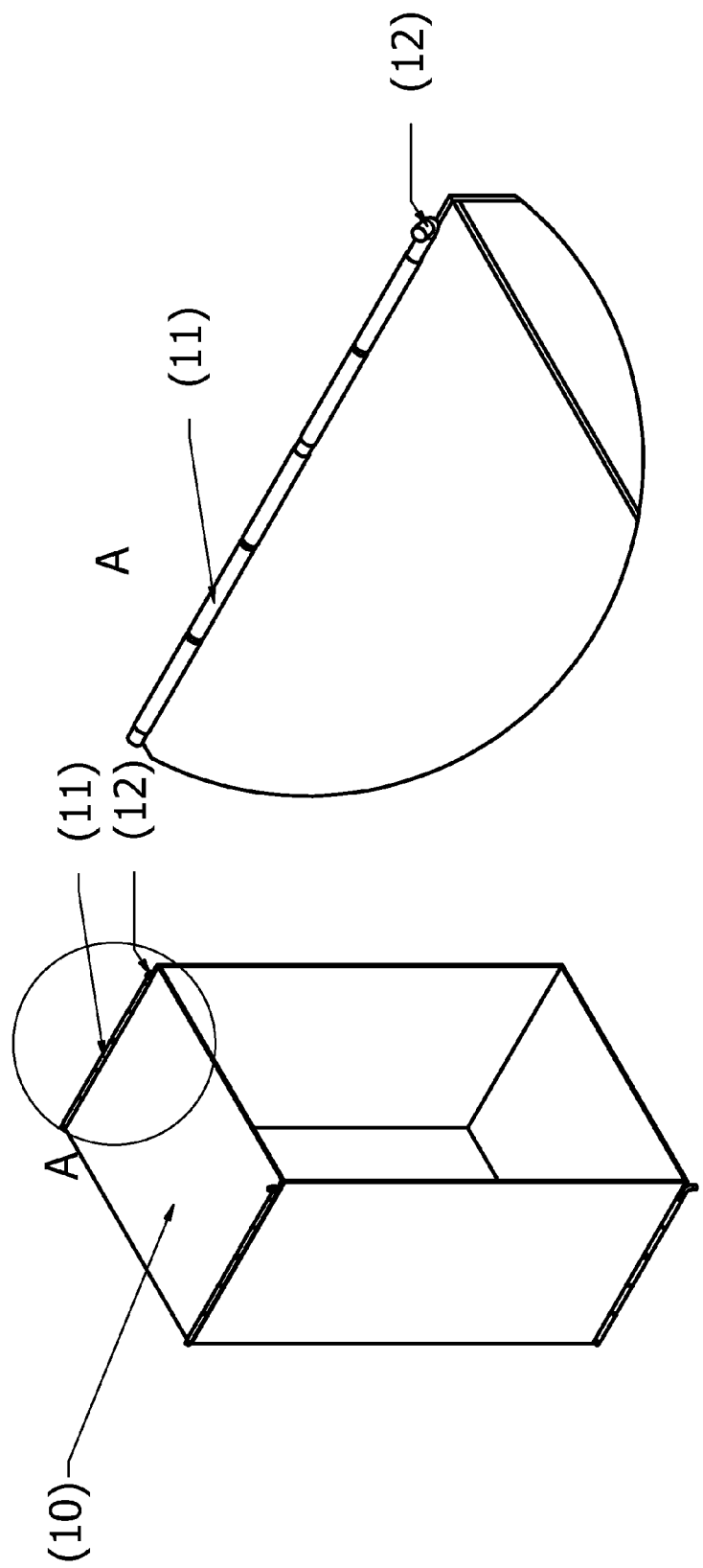
FIG. 2 shows the support for the substrate containing boxes, according to the present invention.

FIG. 1 shows stainless steel pipes with double air expansion device and a mixer for injecting and recirculating air, when the bioreactor is working with forced draft. These pipes are provided with supply valves and fast couplings for easy assembly and cleaning of the pipes.

BEST WAY TO CARRY OUT THE INVENTION

For an optimal running and production of biosubstances, the fixed bed bioreactor with natural convection and forced draft comprises a biotreatment chamber with an air head of 12.5 cm as a preferred measure, three stainless steel boxes that can be disassembled of 25 cm in height, 30 cm in width and 60 cm in depth as a preferred measurement, disposable meshes and a central bed cooling tube; to facing diffusor systems each with a combined positive and negative spin partition walls and a base diffusor with a positive spin dispersion wall for air distribution, a system for accumulating and collecting exudates.

The lid of the bioreactor is provided with a gasket for air tight seal, a top lid with a filter and a mesh for air exchange and control of its concentration, three growth supervision peepholes, two samplers equipped with a hand orifice for taking samples and an accessory that allows to store the sample without letting the material inside the bioreactor contacting the environment.

The bioreactor comprises six thermocouples with an external reading port, which are arranged inside the beds while the equipment is loaded; similarly, it has a device to register relative humidity, with a scale from 5 to 100% and ambient temperature of the chamber inside the bioreactor, having an average capacity of 30 kg of solid substrate.

A variant to the bioreactor is provided by the spinning drum bioreactor with oscillating movement, with natural and forced convection, which comprises a drum or cylindrical chamber containing the substrate, a peephole, thermocouples for measuring temperature of the substrate, a thermo-hygrometer for measuring relative humidity and temperature of the environment inside the chamber; a speed and spin mode control system for oscillation and full rotation of the drum, having a capacity of 10 kg of inoculated substrate. The tray bioreactor with natural convection has a capacity of 100 kg of inoculated substrate and comprises a general chamber containing removable nine trays with a lower support for the substrate, a free air head equivalent to a third of the size of the bioreactor and partition walls that allow to direct the flow of exudate towards a bottom collecting chamber thereof.

Processes for Production of Biosubstances by Solid-State Fermentation with Macromycetes Fungus.

Figure 10:
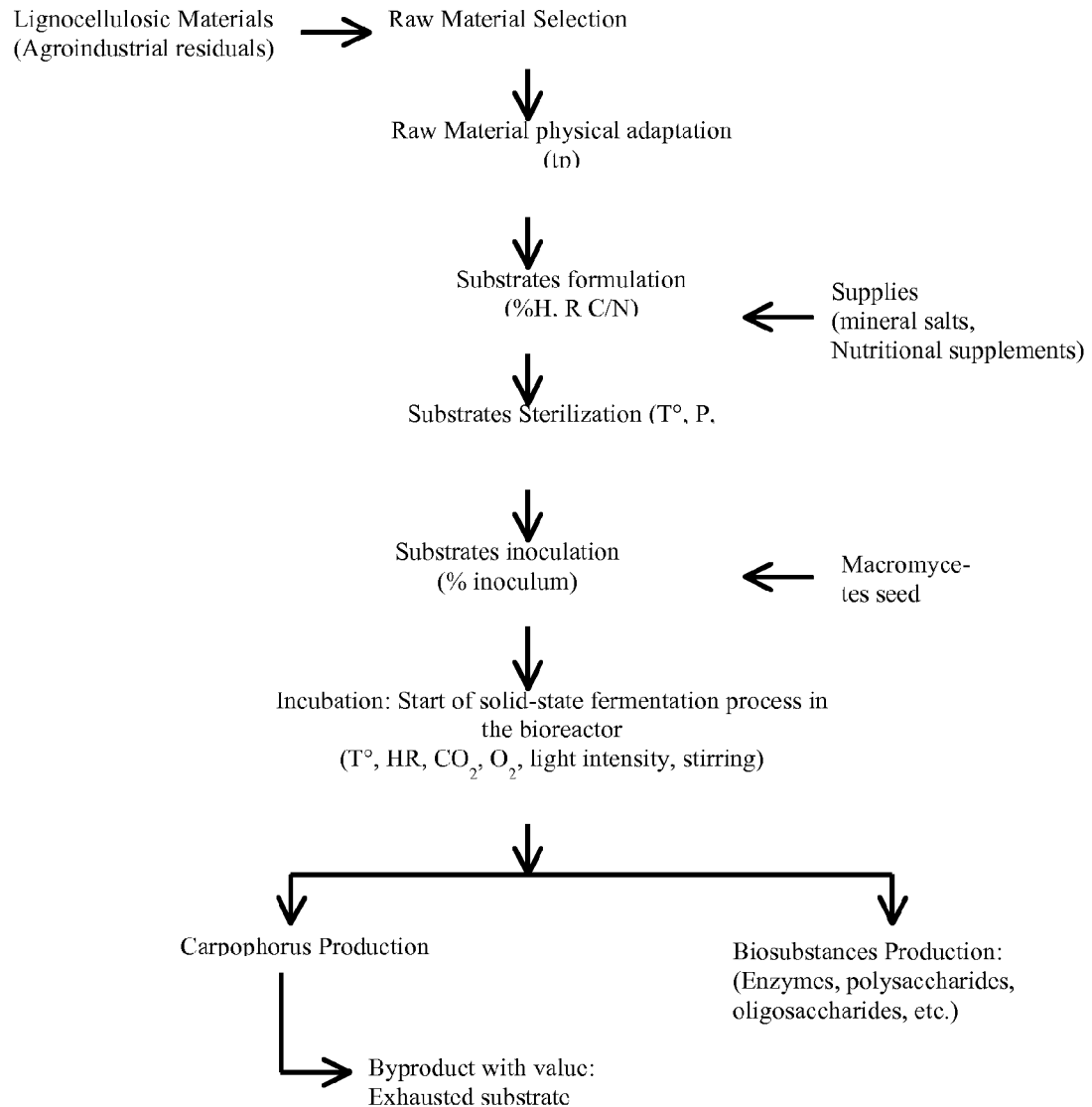
FIG. 10 shows the process of biosubstances production by solid-state fermentation, according to the present invention.

FIG. 10 shows a scheme process of biosubstances production by solid-state fermentation using macromycetes fungi and lignocellulosic residuals as raw material.

The Figure is a process diagram illustrating how to obtain bioactive substance by solid-state fermentation in fixed bed bioreactor with natural convection and forced draught, under controlled conditions using macromycetes fungi.

All the physical and chemical variables of the substrates, the environmental conditions and bioreactor selection depend directly on the species of macromycetal fungi selected, which also produces biosubstances with unique characteristics.

Analysis Result

The biosubstances obtained in the fixed bed bioreactor with natural convection and forced draft have been assessed from the exudates and the colonized solid matter. The enzymatic activities which have been determined for the colonized substrate and the exudate, respectively, are: Endogluconase (ENG) from 8 to 26 mmol/g s.s. min and between 2 and 9 mmol/mL. min, Exogluconase (EXG) from 8-24 mmol/g s.s. min and 1.5-12 mmol/mL. min, b-glucosidase (b-G) from 2-9 mmol/g s.s min and 0.7-2.5 mmol/mL. min, Endoxylanase (ENX) from 12-25 mmol/g s.s. min and 4-9 mmol/mL. min, ligninine peroxidase (LiP) 9-18 mmol/g s.s. min and 2-7 mmol/mL. min, lacase (Lc) from 12-27 mmol/g s.s. min and 5-12 mmol/mL. min, and manganese peroxidase (MnP) from 5-13 mmol/g s.s. min and 1.5-4 mmol/mL. min.

In addition, the total polysaccharides present in the exudates and the solid substrates colonized with macromycetes fungi have been determined to be in the order of 0.03 to 0.13 g/g s.s. in the colonized solid substrate and from 0.2 to 0.8 g/L in the exudates. Similarly, the content of N-acetyl-D-glucosamine (NAGA) has been determined in the solid substrate colonized with each species of macromycetes fungi, which has been obtained in an amount of between 0.04 and 0.13 mg/mg s.s.

The invention claimed is:

1. A bioreactor for obtaining bioactive substances by solid state fermentation using macromycetes fungi, wherein the bioreactor is a fixed bed bioreactor comprising:
a stainless steel bioreactor body having lateral portions with concave shape and an upper opening, wherein an interior space of said bioreactor is accessed via said upper opening;
a base air diffuser positioned inside said interior space, said base diffusor comprising a top portion, a bottom portion and lateral portions extending between said top and bottom portion and a plurality of side-by-side air diffusing panels arranged between said top and bottom portions and longitudinally extending between said lateral portions, wherein said plurality of side-by-side air diffusing panels are inclined at a first angle with respect to said top portion;
a lateral air diffuser positioned inside said interior space comprising a top portion, a bottom portion, concave lateral portions extending between said top and bottom portion and a plurality of side-by-side lateral air diffusing panels arranged between said top and bottom portions and longitudinally extending between said concave lateral portions, wherein a first plurality of said plurality of side-by-side lateral air diffusing panels are inclined at a second angle with respect to said top portion of said lateral air diffuser and a second plurality of said plurality of side-by-side lateral air diffusing panels are inclined at a third angle with respect to the bottom portion of said lateral air diffuser;
a plurality of removable boxes, each of said removable boxes being provided with a hinge and a pin on each side of the box allowing complete disassembling of the box, wherein said removable boxes are positioned side-by-side inside said interior space;
a removable main lid, provided to close the upper opening of said bioreactor body, comprising a plurality of inspecting holes allowing visual access to said interior space and two sets of sampling openings, wherein said main lid further comprises a top opening and a removable top lid provided to control the supply of oxygen and CO2 inside said interior space;
a first valve provided to collect exudates and a second valve provided to clean the bioreactor;
an air mixer having a fresh air inlet, a recirculated air inlet, a mixing tank mixing the air received at the fresh air inlet with the air received at the recirculated air inlet and an air output receiving said mixed air; and
an air injecting element connected between said air output and said bioreactor body.

2. The bioreactor according to claim 1, wherein said lateral air diffuser further comprises a central partition panel extending between the top and bottom portions of said lateral air diffuser across said first and second plurality of said plurality of side-by-side lateral air diffusing panels.

3. The bioreactor according to claim 2, wherein said plurality of side-by-side lateral air diffusing panels distributes the air when the bioreactor operates with natural convection and directs the air flow when the bioreactor operates with forced draft.

4. The bioreactor according to claim 1, wherein each of said plurality of inspecting holes is positioned to allow visual access to a respective removable box.

5. The bioreactor according to claim 1, wherein said two sets of sampling openings are positioned apart from each other near lateral sides of said removable main lid.

6. The bioreactor according to claim 1, wherein said removable main lid further comprises a plurality of handles allowing removal of said main lid from said bioreactor body.

7. The bioreactor according to claim 1, wherein said removable top lid further comprises a plurality of handles allowing removal of said top lid from said main lid.

8. The bioreactor according to claim 1, wherein said air injecting element comprises a mixed air inlet connected to the air output of said air mixer and a first pipe directing the air received at said mixed air inlet to a first air expander connected to said bioreactor body.

9. The bioreactor according to claim 8, further comprising a second pipe directing the air received at said mixed air inlet to a second air expander connected to said bioreactor body.

10. The bioreactor according to claim 1, wherein said base air diffuser further comprises a plurality of partition panels extending between the top and bottom portions of said base air diffuser across said plurality of side-by-side air diffusing panels.

11. The bioreactor according to claim 1, further comprising a bottom air diffuser separate from said base air diffuser and said lateral air diffuser, wherein said bottom air diffuser is positioned inside said interior space.

12. The bioreactor according to claim 1, wherein said base air diffuser is provided as a supporting base for said plurality of boxes.

13. The bioreactor according to claim 1, further comprising a second lateral air diffuser facing said lateral air diffuser, wherein both lateral air diffusers are positioned inside said interior space perpendicular to said base air diffuser.

14. The bioreactor according to claim 1, wherein the plurality of side-by-side air diffusing panels distributes the air when the bioreactor operates with natural convection and directs the airflow when the bioreactor operates with forced draft.

15. The bioreactor according to claim 1, further comprising a sample holder having a main container including a first handle and a first window for taking samples; a valve including a second window and a second handle for controlling the flow of external air into the bioreactor; and a general holder containing said sampler holder and having a third window for allowing access into said bioreactor.

16. The bioreactor according to claim 1, further comprising a temperature monitor, a relative humidity monitor, a thermocouple selector, on/off indicator lights, and a main switch.

* * * * *